United States Patent [19]

Sittler et al.

[11] Patent Number: 4,869,282

[45] Date of Patent: Sep. 26, 1989

[54] MICROMACHINED VALVE WITH POLYIMIDE FILM DIAPHRAGM

[75] Inventors: Fred C. Sittler, Victoria; Cynthia R. Nelson, Anoka, both of Minn.

[73] Assignee: Rosemount Inc., Eden Prairie, Minn.

[21] Appl. No.: 282,432

[22] Filed: Dec. 9, 1988

[51] Int. Cl.$^4$ .................. F16L 55/18; F16K 11/00
[52] U.S. Cl. .................................. 137/15; 137/315;
137/863; 251/367; 251/368; 251/61.1
[58] Field of Search ............... 137/863, 253, 209, 92,
137/838, 15, 315; 251/61.1, 368, 367; 29/157.1 R

[56] References Cited

U.S. PATENT DOCUMENTS

| | | | |
|---|---|---|---|
| 3,889,711 | 6/1975 | Hirao | 251/61.1 |
| 3,934,611 | 1/1976 | Gachot et al. | 251/61.1 |
| 4,119,120 | 10/1978 | Mahaffy | 137/888 |
| 4,203,128 | 5/1980 | Gackel | 357/60 |
| 4,304,260 | 12/1981 | Turner et al. | 251/61.1 |
| 4,333,500 | 6/1982 | Broerman | 137/863 |
| 4,471,647 | 9/1984 | Jerman | 73/23.1 |
| 4,562,724 | 1/1986 | Scott | 137/253 |
| 4,581,624 | 4/1986 | O'Connor | 357/26 |
| 4,647,013 | 3/1987 | Giachino | 251/331 |
| 4,676,897 | 6/1987 | Kuze | 210/198 |
| 4,756,508 | 7/1988 | Giachino et al. | 251/368 |
| 4,768,751 | 9/1988 | Giachino | 251/331 |

OTHER PUBLICATIONS

Silicon Micromechanical Devices by James B. Angell et al., Scientific American V 248, N 4, Apr. 1983, pp. 44-45.

Primary Examiner—A. Michael Chambers
Attorney, Agent, or Firm—Kinney & Lange, P.A.

[57] ABSTRACT

A micromachined miniature valve used for gas chromatography has very low valve and interconnection dimensions to reduce the fluid volume inherent in other gas switching valves to thereby provide accurate measurements involving small gas flows. In order to reduce actuating diaphragm size, without encountering excessive stress concentrations in the diaphragm, the diaphragm can be polyimide film actuated in connection with a silicon valve body having valve seats with ports that are opened or closed by deflection of the diaphragm. Silicon wafers can be micromachined using batch fabrication techniques to provide the necessary valve seats and passageways for operating. The valve assembly is produced as a layered sandwich made up of individual wafers, including an actuator layer, a stop layer, a valve seat layer, and a layer which has flow channels receiving gas from the valve seat layer and making the necessary interconnections to provided outlets. The diaphragm film is positioned between the valve seat layer and the stop layer, and is deflected or displaced to control passage of gases through the valve openings. The diaphragm layer is sealed to the silicon valve body by a process which involves fusing, such as glass frit or solder sealing.

22 Claims, 2 Drawing Sheets

MICROMACHINED VALVE WITH POLYIMIDE FILM DIAPHRAGM

BACKGROUND OF THE INVENTION

1. Field of the Invention

The present invention relates to miniature, micromachined valves which provide reduced fluid volume in the valve and are useful for gas chromatography.

2. Description of the Prior Art

In the prior art various miniature, micromachined valves have been advanced. The valves are made using chemical etching or micromachining techniques for forming passageways in single crystal silicon wafers which are then bonded into a sandwich or layered construction. The valves are generally opened and closed by actuating a silicon deflecting diaphragm, usually by electrostatic control or by fluid pressure actuation. Miniaturization is desired, but if the diaphragm size is reduced substantially, the stress levels in the diaphragm become excessively high when the diaphragm is actuated sufficiently to fully open the valves, particularly when silicon is used. The absence of a relatively flexible, low stress level material that can be utilized as a diaphragm and which will withstand the hostile environment in which the valves operate has limited the reduction in size of the valves. Deflections in the range of 0.002 to 0.003 inch (50–75 microns) must be achieved without overstressing the diaphragms. The present invention relates to a batch fabricated, sandwich construction valve utilizing silicon, glass or other suitable material wafers that are micromachined or molded to form necessary ports and channels, and a diaphragm film between two wafers for actuating the valves formed in the layers.

SUMMARY OF THE INVENTION

The present invention relates to a micromachined valve which has a low fluid volume, and which operates reliably for use in gas chromatography. Silicon wafers can be micromachined to make valve passageways and openings in a batch process utilizing known micromachining techniques, such as photolithography and etching, electrostatic discharge machining, or other known techniques. If glass layers are used, the channels or passageways can be molded in place. The precision of such micromachining techniques insures that very small valve seats can be made, and a substantial number of passageways, channels, or openings also can be formed on various wafers.

The valve of the present invention utilizes an organic diaphragm layer that will permit at least a 0.002 inch deflection of a small diameter diaphragm over a valve seat in order to fully open the valve to minimize pressure drop across the valve without being overstressed or breaking from fatigue failure. The organic diaphragm layer or film operates across a wide temperature range, and can be joined (bonded) to the silicon wafers used for forming the valve components with a glass frit or solder so that a permanent fused bond is obtained and the upper operating temperature is not limited by use of adhesives.

The organic diaphragm film withstands the high temperatures required for using glass frit or solder bonding, and the organic film's mechanical properties of stress in relation to deflection allow significant reductions to the overall valve size compared to valves made with traditional metal or semi-conductor diaphragms. Further, the organic film can be metallized to produce a moisture barrier and enhance its chemical resistance. By also depositing metal on the silicon wafer forming the valve seats, the surfaces in contact between the metallized diaphragm and metallized silicon form a metal to metal seal to improve the valve sealing characteristics.

Gas chromatography valves are used for fluid sample injecting, back flushing, stripping and similar controlled flow processes and minimum fluid volume in the valve body is desired to avoid deleterious results from mixing a new sample with old gas remaining in the valve passages.

The present design shown shows a six port valve for illustrative purposes. The design can easily include configurations for 1 or more valves. The size constraints are reduced because of the use of an organic film with a high temperature melting point and low stress characteristics. Low cost, reliable operation is achieved, small valve sizes.

The component layers of the valve are formed to provide flow channels, valve seats and ports in the same manner that is done when silicon diaphragms are utilized. In this invention, the diaphragms are formed with a sheet of organic material, which is sealed by fusing around the individual valve seats, and when operated provides adequate clearance to minimize pressure drops and to minimize the fluid volumes in the valve by keeping the size extremely small.

A valve controlling fluid flow comprises a brittle layer having a cavity formed therein surrounding a valve seat which can be covered to control fluid flow through the cavity. The cavity opens to a first planar surface on the brittle layer. A second layer has a second planar surface facing, but spaced away from, the first planar surface. The second layer includes forcing means aligned with the seat for exerting a control force. A sheet sandwiched between the first and second planar surfaces forms a diaphragm actuated by the control force and overlying the seat. The control force deflects the diaphragm for selectively covering the seat to control fluid flow. The sheet is formed of a flexible organic material, preferably a polyimide such as Kapton material, fused to the brittle layer to form a fused seal around the cavity. The fusing can be accomplished by frit sealing or soldering. The valve seat surrounds a first passageway formed in the brittle layer for carrying the fluid flow. A second passageway formed in the brittle layer for carrying the fluid flow opens to the cavity. Fusing means are disposed between the brittle layer and the sheet for forming the fused seal. The brittle layer is preferably formed of a material comprising silicon in which the cavity is etched.

DETAILED DESCRIPTION OF THE PREFERRED EMBODIMENT

Figure 3:
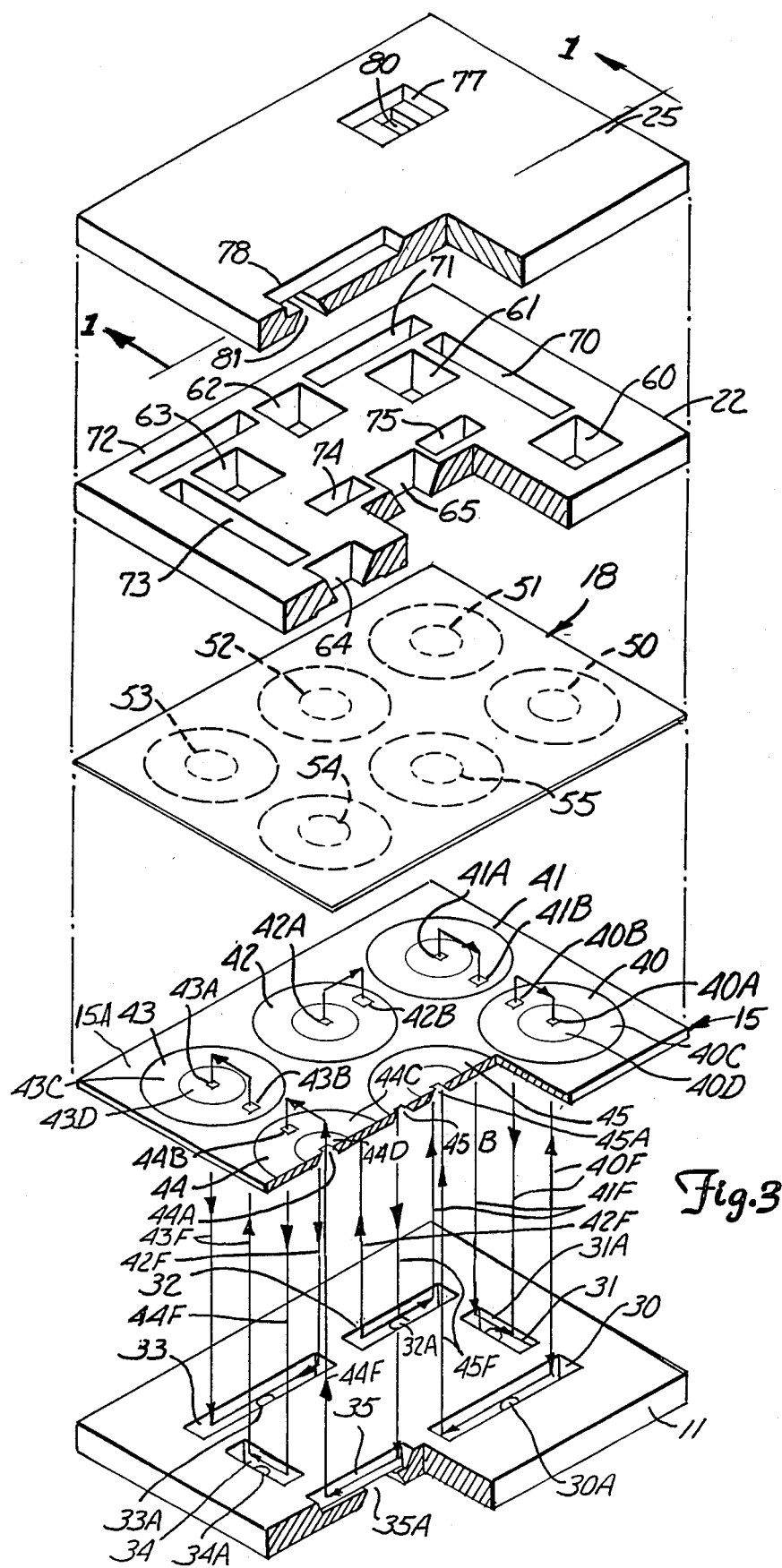
FIG. 3 is an exploded view of a valve made according to the present invention and shown with arrows to illustrate flow paths through sets of valves in two different actuation modes.

A miniature valve assembly indicated generally at 10 made according to the present invention comprises a sandwich construction of several individual layers bonded together, including a base flow channel layer 11, a valve seat wafer or layer 15 having a planar surface 15A, a diaphragm layer 18,, a stop layer 22 having one surface for controlling deflection of diaphragms away from valve seats and for providing control fluid pressure passageways and ports, and an actuator passageway connection layer 25. The base flow channel layer 11 has six flow channels as shown in FIG. 3, indicated at 30, 31, 32, 33, 34, and 35 and these channels are oriented to be sufficiently long to fluidly connect two orifices or passageways from each of the individual valves on valve seat layer 15 to ports on the base flow channel layer 11. The valve seat cavities are shown at 40, 41, 42, 43, 44, and 45, and the two orifices or passageways for each valve seat cavity are also indicated at 40A–45A and 40B–45B, respectively.

The valve seat cavities 40–45 are formed on the valve seat layer 15 in a suitable manner such as etching. The valve seat cavities are formed as annular recesses 40C–45C, that define central bosses or valve seats 40D–45D that have upper surfaces coplanar with the original upper surface of the layer 15 surrounding each of the recesses.

The flow channels 30, 31, 32, 33, 34 and 35 are formed only partway through the channel layer 11, and each of the flow channels has a port or opening indicated at 30A, 31A, 32A, 33A, 34A, and 35A that opens to the side of the channel layer 11 opposite from the valve seat layer 15. Suitable gas conduits (not shown) are connected to each of the individual ports 30A–35A on the outwardly facing surface of the base flow channel layer 11.

Figure 1:
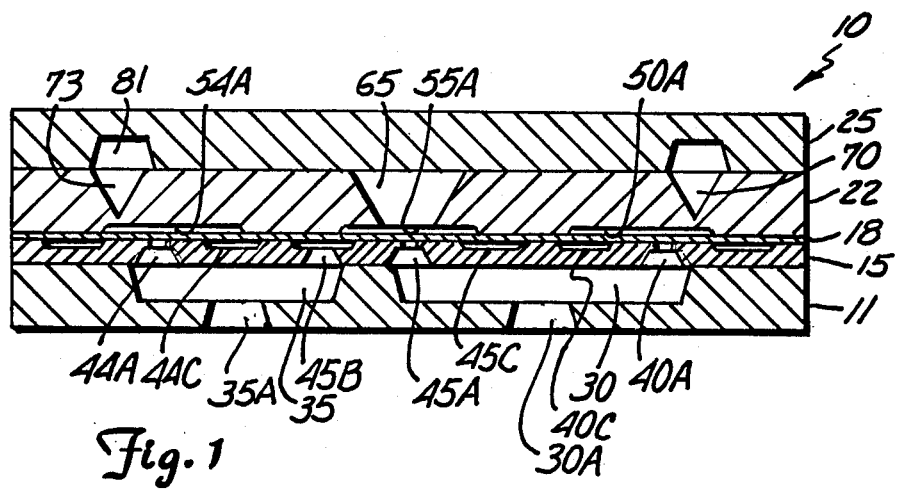
FIG. 1 is a vertical sectional view of a typical sandwich construction for a valve utilizing a diaphragm made according to the present invention and taken along line 1—1 in FIG. 3.
Figure 2:
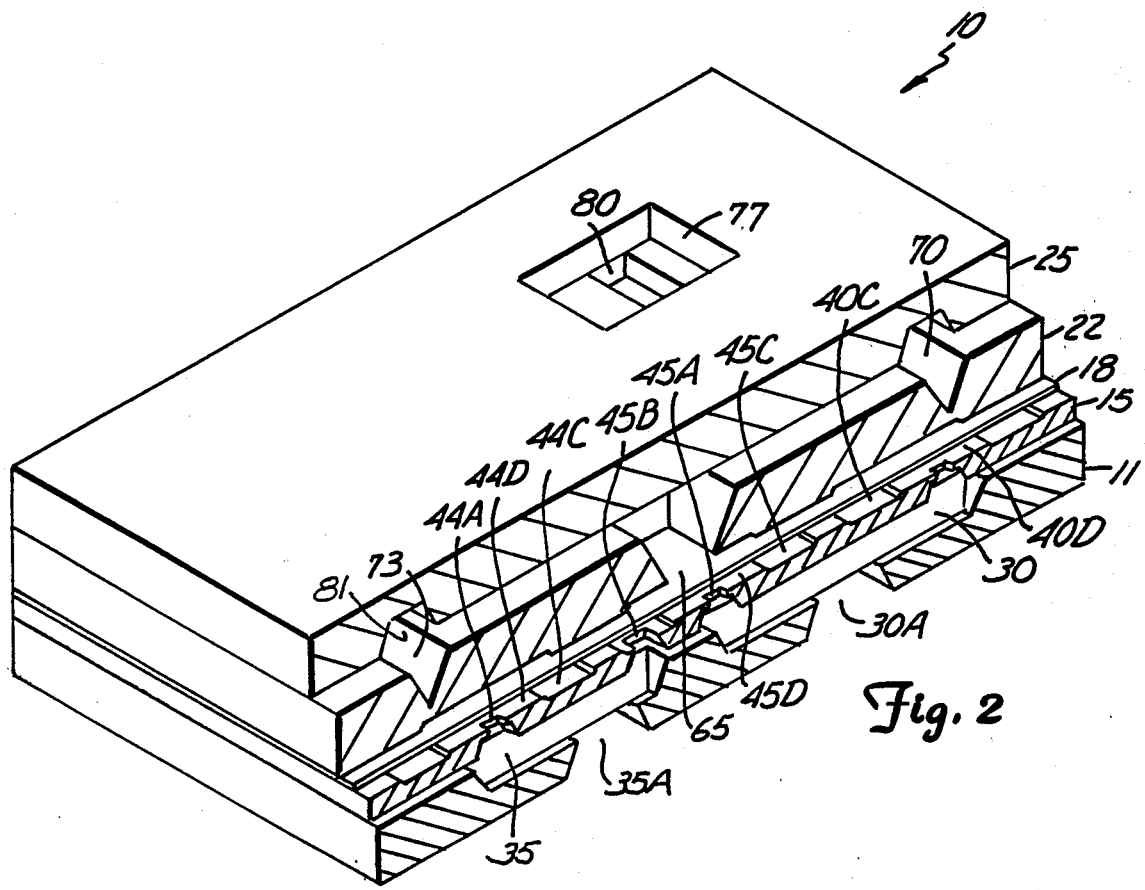
FIG. 2 is a schematic perspective sectional view with the individual layers broken back from the section line of FIG. 1 showing the valve having a diaphragm made according the the present invention.

Each of the valve seats 40D–45D is made so that the sealing surfaces are on a side thereof opposite from the base flow channel layer 11. The valve seat sealing surfaces are the top plane surfaces of the bosses 40D–45D formed by recesses 40C–45C. In some applications, the bosses 40D–45D are not needed and the sealing surface or valve seat can be the central region of the cavity. The diaphragm layer is bonded to the valve seat layers around the periphery of each of the recesses. When pressure is applied to the diaphragm layer at a location above a diaphragm section overlying a respective valve seat, the diaphragm section will deflect down against the underlying sealing surfaces of the valve seat and close the associated valve orifice. The control for the individual diaphragm sections of the diaphragm layer is achieved by having stop layer 22 provided with appropriate channels that provide pressure over the individual diaphragm sections. In FIG. 3, these diaphragm sections are represented by dotted lines, and are indicated at 50, 51, 52, 53, 54 and 55, respectively. They overlie the respective valve seats 40D–45D. The diaphragm and stop layer 22 are bonded together in regions surrounding the diaphragm sections. Recesses in stop layer 22, shown at 50A, 54A and 55A in FIG. 1 overlie each valve seat. A control pressure input port 65 is shown as well and as will be explained, pressure at port 65 will cause diaphragm section 55 to deflect and close flow through valve seat 45D and also close other valves connected to be selected for simultaneous actuation with diaphragm 55 with valve seat 45.

The central or axial port 40A–45A of each valve seat cavity 40–45 forms the flow control port for that valve seat and is closed by actuation of the associated diaphragm. The second port 40–45B of each valve seat is an outer peripheral port. The outer peripheral ports are oriented at different radial locations in different valve seats, in order to provide communication between selected ones of the channels 30–35, as desired.

The stop layer 22 is provided with six control ports, namely, 60, 61, 62, 63, 64, and 65 therethrough, which correspond to the diaphragm sections 50–55. These are open to provide fluid to the individual diaphragm sections for exerting a control force to deflect the diaphragms. Beneath each of these ports is a recess that is defined in the surface of the stop layer facing the diaphragm layer 18, such as those indicated at 50A, 54A and 55A. These recesses overlie the active portion of the diaphragm sections and overlie the bosses or valve seats 40D–45D. The recesses are of sufficient depth so that the diaphragm sections will deflect away from the respective underlying ports on the bosses of the respective valve seat to provide adequate clearance for gas flow. As stated this deflection will be generally in the range of 0.002 inches (50 microns). The diaphragm sections 50–55 are clamped around their peripheries between the valve seat layer and the stop layer.

In addition, the stop layer 22 has channels in the upper side thereof that are used for directing actuating fluid to the control ports for the respective diaphragm sections 50–55 on the diaphragm layer 18. These channels are indicated at 70, 71, 72, 73, 74 and 75. These channels do not extend all the way through the stop layer 22, but rather are V shaped channels that are etched in place for providing the appropriate flow path for actuator fluid in combination with flow channels defined in the undersurface of layer 25.

The actuator layer 25 includes exterior ports 77 and 78, respectively, and passageways such as those shown at 80, and 81 in the lower surface, so that when one of the ports 77 or 78 is connected to a control pressure fluid (the controls are such that normally only one of ports 77 or 78 is operated at time), three of the diaphragm sections 50–55 would be held closed, and the other three would be permitted to open. The unit is set up so that every other valve is operated to direct the flows in the appropriate direction through the ports 30A–35A and the channels 30–35. Thus, with ports 78 under pressure, diaphragm sections 50, 52 and 54 will be deflected to close the underlying ports 40A, 42A and 44A. When port 77 is provided with control pressure, diaphragm sections 51, 53 and 55 will be deflected to close the underlying ports 41A, 43A and 45A while the other valves are permitted to open to flow.

When the valve assembly is made, the layers are micromachined, such as through the use of photolithographic techniques and etching (except for the diaphragm) or the various channels and passageways or ports can be formed by electrostatic discharge machining (EDM) and in some instances, if glass layers are utilized, the channels could be molded in place when the lass layers are formed.

The type of machining utilizes standard techniques. The materials can be any desired semi-conductor materials or other brittle materials that are non-reactive to the gases used. A material that is useful for the channel layer, the valve seat layer, the stop layer, and the actuator layer is silicon, which can be etched and which is inert to the various gases being handled by the valve assembly 10. Other materials such as glass or sapphire also could be used for one or more of the layers. The layers do not have to be all one type of material.

The diaphragm layer 18 can be metallized, and then when the valve assembly layers are joined together into a sandwich, the diaphragm sections 50–55, and the areas circumscribed within the dotted lines that overlie the respective valve seats 40–45 are not joined to the stop layer or the valve seat layer. The diaphragm layer borders at the interface of the joining layers surrounding the valve seats, so that the diaphragms are sealed completely from one another. The deflection away from the ports of the valve seat against the stop layer recesses is controlled by the depth of the recesses in the stop layer so that deflection can be held within a desired range that will insure proper clearance, but will not cause failure of the diaphragm.

A Kapton polyimide film diaphragm can be metallized. Glass frits can be used to provide operation across a wide range of temperature from more than −200° C. to +400° C.

A permanent bond is achieved utilizing glass frits, particularly when silicon layers are sandwiched against the diaphragm layer. The temperature limits of the valve are thus quite wide.

As shown, the valve seats have a boss in the center, surrounding the center ports 40A–45A, which also can be metallized, and when the diaphragm layer is metallized, a metal-to-metal valve-diaphragm seal can be obtained.

By way of operation, the valve as exemplified herein can be made so that pressure is exerted from the actuator port 77, and through the appropriate channels such as 74 and 75 control pressure is present at ports 61, 63 and 65 so that the valve diaphragm sections 51, 53 and 55 will be forced against the respective valve seat bosses 41D, 43D and 45D to close off the central ports 41A, 43A and 45A. The diaphragm sections 50, 52 and 54 are relaxed, so that pressure acting through either of the ports of those respective valve seats 40, 42 and 44 aligned with those diaphragm sections will permit flow through the valves. The direction of flow depends on pressure differentials at the ports connected to the channels that are connected by those valve seats. For example, if the port 30A is carrying a fluid under pressure that is higher than that in port 31A, the valve 40 will be permitted to open so that fluid can flow as shown by the arrow 40F through port 40A and then through port 40B back to channel 31 and out through port 31A.

Likewise, if the pressure in port 32A is higher than that in port 33A, the channel 32 will connect port 42B to the port 42A and fluid will flow from the channel 32 as shown by arrows 42F into the channel 33 and out port 33A.

If the pressure in channel 35 is higher than that at port 34A of channel 34, because valve 44 will be permitted to open, fluid will flow as shown by arrow 44F through the port 44A, and out port 44B into the channel 35 and then out passageway 35A to its intended location.

When the controls are such that control pressure is present at port 78, and not at port 77, channels 70, 71, 72 and 73 and interconnections in the actuator layer provide control pressure at ports 60, 62 and 64 and diaphragm sections 50, 52 and 54 will be deflected so the valve port in valve seats 40, 42 and 44 will be closed. Fluid under pressure can then flow through the ports of valve seats 41, 43 and 45 because those diaphragm sections are relaxed. Then, for example, if the pressure at port 31A is still the exit port and the pressure in channel 32A is high, fluid will flow as shown by arrow 41F through the port 41A, and out the port 41B from channel 32 to channel 31. If the pressure is higher in channel 34 than it is in channel 33, fluid will flow, as shown by arrows 43F, in through port 43B and out port 43A and into the channel 33, for a flow path connecting the two channels 33 and 34.

If the pressure in channel 30, and specifically at port 30A is greater than that in channel 35, and specifically at port 35A, fluid will flow as shown by arrows 45F through the valve seat 45 in through port 45A, and then through port 45B into the channel 35 and out port 35A.

By alternate actuation, a variety of different flow directions can be obtained by connecting the channels 30–35 in the channel layer 11.

The Kapton film diaphragm is important to operation by keeping the diameter of the valve seats small.

The overall size of the die shown is generally in the range of about 0.5 inch (10 millimeter), and the active area of the respective diaphragm sections 50–55 in relation to the needed diaphragm thickness can be kept very low without overstressing the Kapton film.

The center to center distances between the valve seats can be reduced to a very small dimension by using the Kapton diaphragm layer. The fluid volume of the present valve can be reduced to about one-third of the previous devices. The Kapton diaphragm has a long fatigue life, and can be fritted into place in the batch fabrication process. The polyamide diaphragm can be gold plated, to allow reflow solder melting for bonding as well. The Dupont Kapton material is able to withstand these fusing processes because Kapton has a higher melting temperature than the solder or frit. The actuator layer interconnects with pneumatic controls, and then the second layer provides a stop for the Kapton film to prevent the diaphragm sections from being overstressed. Six ports are utilized for connection through the channels in the channel layer 11, and the Kapton film permits a very favorable ratio of diaphragm diameter to displacement. For example, 0.003 inch diaphragm deflection can be achieved with a diaphragm having a diameter of about 0.130 inch. This gives a ratio of 43:1, and the ratio of diameter to displacement can range between 130:1 and 1:1, which is substantially higher than that of steel. A ratio of tensile strength to Young's modulus is very favorable with the Kapton film material, and 0.002 to 0.003 inch deflection can easily be obtained without overstressing. Substantial difficulty is encountered in trying to individually fabricate these small valves, but by using batch fabrication techniques and micromachining, the valves can be quickly made. There is no need for individual discrete assembly, and with the metallized Kapton film surface in the area of the seal, and metallizing the seat surfaces (which are on a silicon layer) gives a very good metal to metal seal. The valve has the ability to take very high line pressures because of the stop layer provided.

An extra layer of Nichrome plating in the frit area may be added to enhance the fritting bond.

Although the present invention has been described with reference to preferred embodiments, workers skilled in the art will recognize that changes may be made in form and detail without departing from the spirit and scope of the invention.

What is claimed is:

1. A valve controlling fluid flow, comprising:

a brittle layer having a cavity formed therein surrounding a valve seat which can be covered to control fluid flow through the cavity, the cavity opening to a first planar surface on the brittle layer;

a second layer having a second planar surface facing, but spaced away from, the first planar surface, the second layer including forcing means aligned with the seat for exerting a control force; and a sheet sandwiched between the first and second planar surfaces to form a diaphragm actuated by the control force deflecting the diaphragm for selectively covering the seat to control fluid flow; the sheet being formed of a flexible organic material joined to the brittle layer with a seal fused in place at elevated temperatures and surrounding the cavity.

2. The valve of claim 1 wherein a first passageway is formed in the brittle layer for carrying the fluid flow, the valve seat surrounding the first fluid passageway.

3. The valve of claim 2 wherein a second passageway is formed in the brittle layer for carrying the fluid flow, the second fluid passageway opening to the cavity.

4. The valve of claim 3 further comprising fusing means disposed between the brittle layer and the sheet for forming the fused seal at the elevated temperature.

5. The valve of claim 4 wherein the brittle layer is formed of a material comprising silicon and the cavity is etched.

6. The valve of claim 5 wherein the flexible organic layer has a thickness and the diaphragm has a width and the width to thickness ratio is less than 100:1.

7. The valve of claim 6 wherein the width to thickness ratio is on the order of 65:1 or less.

8. The valve of claim 7 wherein the forcing means further comprise means for coupling a control pressure to the diaphragm to deflect the diaphragm to control fluid flow.

9. The valve of claim 8 wherein the second layer further comprises a stop surface disposed over the diaphragm which limits the deflection of the diaphragm away from the valve seat such that stress in the diaphragm is controlled.

10. The valve of claim 9 wherein the controlled fluid flow is a gas flow.

11. The valve of claim 10 wherein the flexible organic material comprises a material which has a melting point that is higher than the fusing temperature of the fusing means.

12. The valve of claim 11 wherein the flexible organic material comprises a polyimide material.

13. The valve of claim 12 wherein the sheet has a surface facing the valve seat which is metallized.

14. The valve of claim 13 wherein the valve seat is metallized to provide a metal-to-metal seal when the valve is closed.

15. The valve of claim 14 wherein the organic material is Kapton material.

16. The valve of claim 15 wherein the fusing means comprise a glass frit.

17. The valve of claim 15 wherein the fusing means comprises a solder.

18. The valve of claim 1 wherein the second layer is formed of a material comprising silicon.

19. The valve of claim 1 wherein the second layer is formed of an organic material integral with the sheet of organic material.

20. The valve of claim 1 wherein said elevated temperatures for forming the fused seal are greater than the working range of 400° C. and below the melting point of the flexible organic material forming the sheet.

21. A valve controlling fluid flow, comprising:

a brittle layer having a micromachined cavity formed therein surrounding a valve seat which can be covered to control fluid flow through the cavity, the cavity opening to a first planar surface on the brittle layer;

a second layer having a second planar surface facing, but spaced away from, the first planar surface, the second layer including forcing means aligned with the seat for exerting a control force; and a sheet sandwiched between the first and second planar surfaces to form a diaphragm actuated by the control force deflecting the diaphragm for selectively covering the seat to control fluid flow; the sheet being formed of a flexible organic material joined to the brittle layer with a nonadhesive seal fused in place at an elevated temperature sufficient for selectively providing one of a frit seal and a solder seal, said fused seal surrounding the cavity.

22. A method for forming a micromachined valve in a batch process including providing a layer of silicon material, micromachining a plurality of cavities which open to a first planar surface on the silicon layer and providing a valve seat formed in the cavity;

supporting a sheet over the first planar surface to form a diaphragm, said sheet being formed of a flexible organic material;

fusing the sheet to the silicon layer with a nonadhesive seal, by fusing the sheet and silicon layer at an elevated temperature, with the fused seal surrounding the cavity; and providing a second layer having a second planar surface on an opposite side of the sheet from the brittle layer, said second layer including forcing means aligned with the seat in the brittle layer for exerting a control force on the sheet fused into place on the brittle layer.

* * * * *

UNITED STATES PATENT AND TRADEMARK OFFICE
CERTIFICATE OF CORRECTION

PATENT NO. : 4,869,282
DATED     : September 26, 1989
INVENTOR(S) : Fred C. Sittler et al.

It is certified that error appears in the above-identified patent and that said Letters Patent is hereby corrected as shown below:

Column 4, line 42, after "operated at" insert --a--.

Column 4, line 61, delete "lass" and insert --glass--.

Signed and Sealed this

Twenty-third Day of October, 1990

Attest:

HARRY F. MANBECK, JR.

*Attesting Officer*           *Commissioner of Patents and Trademarks*